(12) United States Patent
Mori et al.

(10) Patent No.: US 8,593,142 B2
(45) Date of Patent: Nov. 26, 2013

(54) AUTOMATED FIBER TRACKING OF HUMAN BRAIN WHITE MATTER USING DIFFUSION TENSOR IMAGING

(75) Inventors: Susumu Mori, Ellicott City, MD (US);
Jiangyang Zhang, Baltimore, MD (US);
Kegang Hua, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 571 days.

(21) Appl. No.: 12/743,169

(22) PCT Filed: Jan. 5, 2009

(86) PCT No.: PCT/US2009/000011
§ 371 (c)(1),
(2), (4) Date: May 14, 2010

(87) PCT Pub. No.: WO2009/088965
PCT Pub. Date: Jul. 16, 2009

(65) Prior Publication Data
US 2010/0244834 A1    Sep. 30, 2010

Related U.S. Application Data

(60) Provisional application No. 61/009,913, filed on Jan. 3, 2008.

(51) Int. Cl.
*G01V 3/00*    (2006.01)
(52) U.S. Cl.
USPC ........................................................ 324/309
(58) Field of Classification Search
USPC ................................................. 324/300–322
See application file for complete search history.

(56) References Cited

U.S. PATENT DOCUMENTS

| | | | |
|---|---|---|---|
| 5,539,310 A | 7/1996 | Basser et al. | |
| 6,526,305 B1 | 2/2003 | Mori | |
| 6,740,883 B1 | 5/2004 | Stodilka et al. | |
| 7,324,842 B2 * | 1/2008 | Dale et al. | 600/407 |
| 8,140,144 B2 * | 3/2012 | Dale et al. | 600/410 |
| 2003/0013951 A1 | 1/2003 | Stefanescu et al. | |
| 2003/0139659 A1 | 7/2003 | Dale et al. | |
| 2004/0122790 A1 | 6/2004 | Walker et al. | |

OTHER PUBLICATIONS

Mori, S. et al. "Three Dimensional Tracking of Axonal Projections in the Brain by Magnetic Resonance Imaging," Annal. Neurol. 45, vol. 2, pp. 265-269, Feb. 1999.

(Continued)

*Primary Examiner* — Dixomara Vargas
(74) *Attorney, Agent, or Firm* — Venable LLP; Henry J. Daley; Thomas A. Negley

(57) ABSTRACT

A magnetic resonance imaging (MRI) system, comprising: a MRI scanner; a signal processing system in communication with the magnetic resonance imaging scanner to receive magnetic resonance (MR) signals for forming magnetic resonance images of a subject under observations; a data storage unit in communication with the signal processing system, wherein the data storage unit contains database data corresponding to a soft tissue region of the subject under observation. The database data includes information identifying at least one soft tissue substructure encompassed by the soft tissue region of the subject under observation. The signal processing system is adapted to process MR signals received from the MRI scanner to automatically identify at least one soft tissue substructure encompassed by the soft tissue region of the subject under observation.

37 Claims, 16 Drawing Sheets

(56) References Cited

OTHER PUBLICATIONS

Xue, R. et al., "In Vivo Three-Dimensional Reconstruction of Rat Brain Axonal Projections by Diffusion Tensor Imaging," Magnetic Resonance Med. 42, pp. 1123-1127, 1999.

Pruessmann et al., "SENSE: Sensitivity Encoding for Fast MRI," Magnetic Resonance Med. 42, pp. 952-962, 1999.

Pierpaoli and Basser, "Toward a Quantitative Assessment of Diffusion Anisotropy," Magnetic Resonance Med. 36, pp. 893-906, 1996.

Woods et al., "Automated Image Registration: I. General Methods and Intrasubject, Intramodality Validation," J. Comput. Assist. Tomogr. vol. 22, No. 1, pp. 139-152, Jan./Feb. 1998.

* cited by examiner

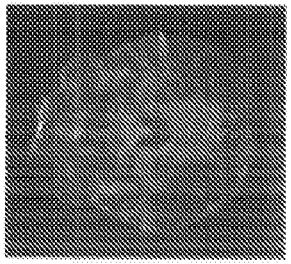
FIG. 5A  z=60
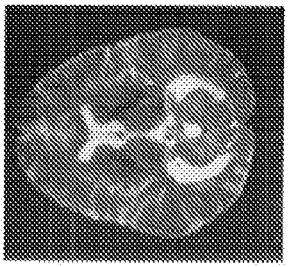
FIG. 5B  z=80
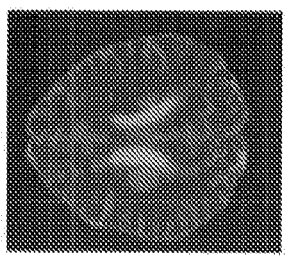
FIG. 5C  z=100
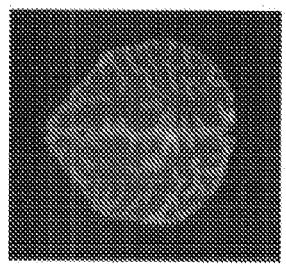
FIG. 5D  z=120 ial Appli- workstation in communication with a data storage unit,

AUTOMATED FIBER TRACKING OF HUMAN BRAIN WHITE MATTER USING DIFFUSION TENSOR IMAGING

CROSS-REFERENCE OF RELATED APPLICATION

This application claims priority to U.S. Provisional Application No. 61/009,913 filed Jan. 3, 2008, the entire contents of which are hereby incorporated by reference.

The U.S. Government has a paid-up license in this invention and the right in limited circumstances to require the patent owner to license others on reasonable terms as provided for by the terms of Grant No.: R01AG20012 and P41RR15241, awarded by the National Institutes of Health.

BACKGROUND

1. Field of Invention

The current invention relates to automated identification of soft tissue substructures in a soft tissue region of a human or animal subject in a non-invasive manner.

2. Discussion of Related Art

It is highly desirable to have automated identification of soft tissue substructures in soft tissue regions of a human and possibly animal subject in a non-invasive manner. For example, diagnosing brain pathologies associated with white matter brain tissue can benefit from such automated identification. Three dimensional white matter fiber tract reconstruction based on diffusion tensor imaging (DTI) is becoming a useful tool in research and clinical studies. (See, for example, U.S. Pat. Nos. 5,539,310 and 6,526,305.) Currently, it is the only method to reconstruct trajectories of white matter fiber tracts non-invasively. However, existing methods of fiber reconstruction require a substantial amount of anatomical knowledge of the brain white matter in order to extract only the tract regions of interest. Because a straightforward reconstruction of all white matter yields a huge amount of fiber tracts entangled inside the brain, it does not have practical value in such an unprocessed form. An operator must have a substantial amount of anatomical knowledge of the brain white matter in order to extract a specific tract from the entangled reconstructed fiber tracts or to prune the regions being reconstructed beforehand. However, experienced operators with detailed knowledge of brain white matter anatomy may not be readily available, which may present a bottleneck in the application of fiber reconstruction technology in research and clinical studies. Further, suboptimal quality of diffusion tensor imaging data may hamper the ability of even the experienced operators in using existing methods. Suboptimal quality may result from, for example, breathing motion of the subject during data acquisition. Therefore, there is thus a need for a system and method for automated tracking of fiber tracts in human brain white matter using diffusion tensor imaging.

SUMMARY

An embodiment of the current invention provides a magnetic resonance imaging (MRI) system that has: a MRI scanner; a signal processing system in communication with the magnetic resonance imaging scanner to receive magnetic resonance (MR) signals for forming magnetic resonance images of a subject under observations; a data storage unit in communication with the signal processing system, wherein the data storage unit contains database data corresponding to a soft tissue region of the subject under observation. The database data includes information identifying at least one soft tissue substructure encompassed by the soft tissue region of the subject under observation. The signal processing system is adapted to process MR signals received from the MRI scanner to automatically identify at least one soft tissue substructure encompassed by the soft tissue region of the subject under observation.

Another embodiment of the current invention provides a workstation in communication with a data storage unit, wherein the workstation is adapted to produce database data based on an atlas having at least one magnetic resonance image corresponding to a soft tissue region having a plurality of soft tissue substructures and data encoding at least one soft tissue substructure in the soft tissue region. The workstation includes: a receive engine to receive the atlas and the data; and a registration engine to generate database data including information identifying the at least one soft tissue substructure by transforming the shape, size, and/or orientation of the atlas to that of the encoding data.

Another embodiment of the current invention provides a workstation to process at least one magnetic resonance image from at least one human subject showing a soft tissue region having at least one soft tissue substructure. The workstation has: a receiving engine to receive the at least one magnetic resonance image from the at least one human subject and database data including information identifying the at least one soft tissue substructure; an alignment engine to align the received at least one magnetic resonance image with the received database data; and a processing engine to generate information identifying the at least one soft tissue substructure on the received at least one magnetic resonance image.

Another embodiment of the current invention provides a method to produce database data from an atlas corresponding to a soft tissue region having a plurality of soft tissue substructures and data encoding at least one soft tissue substructure in the soft tissue region. The method includes: receiving the atlas and the encoding data; and generating database data including information identifying the least one soft tissue substructure by transforming the shape, size, and/or orientation of the encoding data to that of said atlas.

Another embodiment of the current invention provides a method to process at least one magnetic resonance image showing a soft tissue region having at least one soft tissue substructure from a human subject by using database data corresponding to the soft tissue region. The method includes: aligning the database data with the at least one magnetic resonance image by transforming the shape, size, and/or orientation of the database data to that of the magnetic resonance image; and processing information from the database data to identify the at least one soft tissue substructure on the at least one magnetic resonance image.

Another embodiment of the current invention provides a computer-readable medium comprising software, which when executed by a computer system, causes the computer system to perform operations to generate database data based on an atlas corresponding to a soft tissue region and data encoding at least one soft tissue substructure in the soft tissue region. The software includes: one or more instructions to transform the shape, size, and/or orientation of the encoding data to the atlas, and one or more instructions to generate database data including information identifying the at least one soft tissue substructure.

Another embodiment of the current invention provides a computer-readable medium containing database data including information identifying at least one soft tissue substructure.

Another embodiment of the current invention provides a computer-readable medium comprising software, which when executed by a computer system, causes the computer system process at least one magnetic resonance image from a human subject showing a soft tissue region having at least one soft tissue substructure. The software includes: one or more instructions to align database data with the at least one magnetic resonance image by aligning the database data with the at least one magnetic resonance image; and one or more instructions to process information from the database data to identify the at least one soft tissue substructure on the at least one magnetic resonance image.

BRIEF DESCRIPTION OF THE DRAWINGS

Further objectives and advantages will become apparent from a consideration of the description, drawings, and examples.

FIGS. 5A-5D show examples of overlays of an exemplary probability map of the CST on $T_2$-weighted images of a multiple sclerosis (MS) patient in the Montreal Neurological Institute (MNI) coordinate at various locations on the z-axis.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated.

Figure 1:
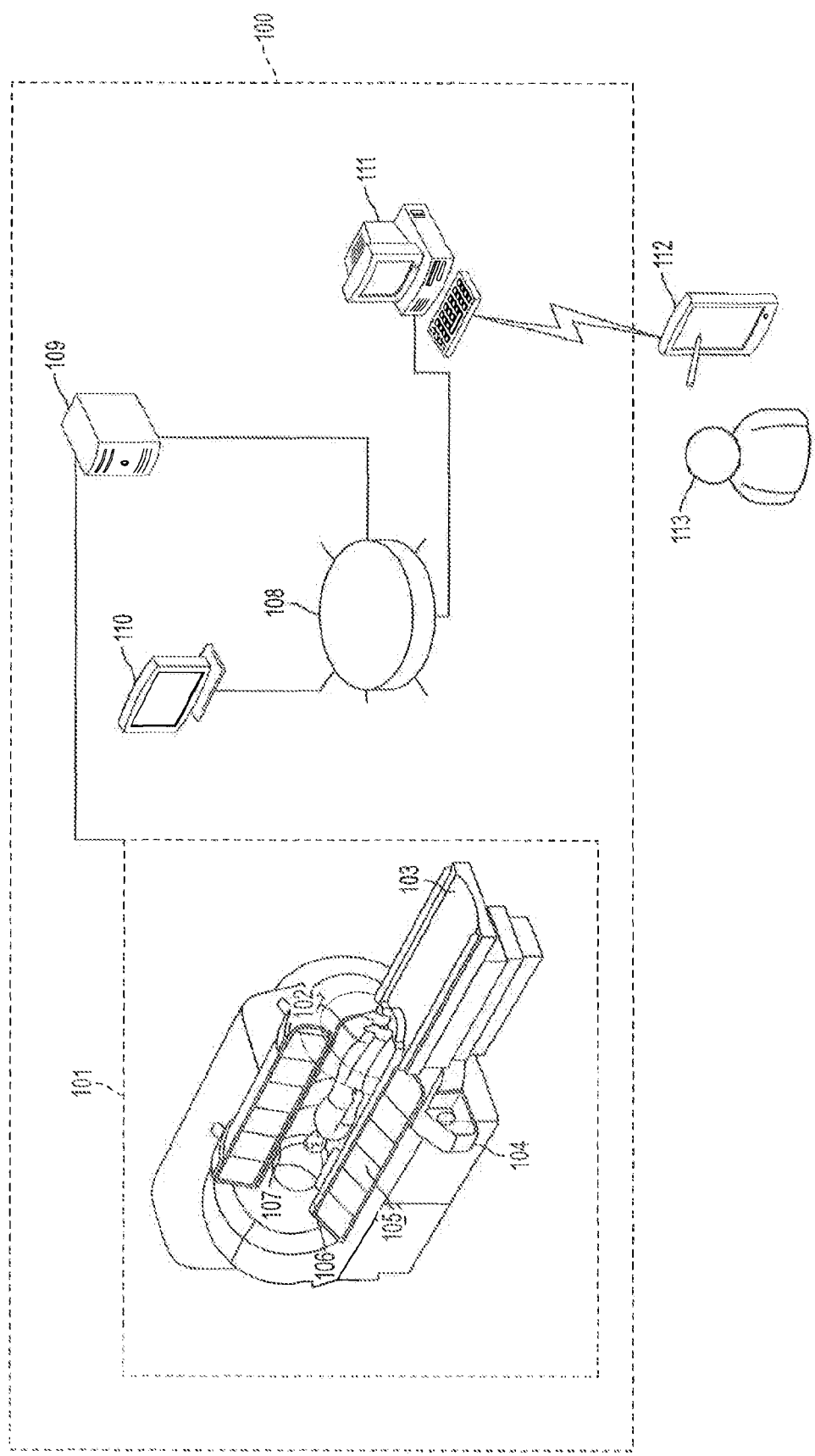
FIG. 1 is a schematic illustration of a magnetic resonance imaging (MRI) system according to an embodiment of the current invention.

FIG. 1 is a schematic illustration of a magnetic resonance imaging (MRI) system 100 according to an embodiment of the current invention. The MRI system 100 has a magnetic resonance scanner 101, a data storage unit 108, and a signal processing unit 109. Magnetic resonance scanner 101 has a main magnet 105 providing a substantially uniform main magnetic field $B_0$ for a subject 102 under observation on scanner bed 103, a gradient system 106 providing a perturbation of the main magnetic field $B_0$ to encode spatial information of the constituent water molecules of subject 102 under observation, and a radio-frequency (RF) coil system 107 to transmit electromagnetic waves and to receive magnetic resonance signals from subject 102.

Data storage unit 108 stores database data corresponding to a soft tissue region of subject 102. The soft tissue region may be, for example, a brain, a heart, a muscle, etc. The database data on data storage unit 108 may include information identifying a soft tissue substructure within the soft tissue region. The soft tissue substructure may be, for example, a brain white matter fiber, a myocardial fiber, a skeleton muscle fiber, etc. The information identifying a soft tissue substructure may be derived from, for example, diffusion tensor magnetic resonance images. The database data may include data from at least one subject that is different from subject 102 under observation. The database data may include data from a previous scan of subject 102 under observation. The term database data is thus defined and shall be understood consistently throughout the confines of this paper.

Data storage unit 108 may be, for example, a hard disk drive, a network area storage (NAS) device, a redundant array of independent disks (RAID), a flash drive, an optical disk, a magnetic tape, a magneto-optical disk, etc. However, the data storage unit 108 is not limited to these particular examples. It can include other existing or future developed data storage devices without departing from the scope of the current invention.

A signal processing system 109 is in communication with magnetic resonance scanner 101 to receive magnetic resonance signals for forming magnetic resonance images of subject 102. Signal processing system 109 may be partially or totally incorporated within a structure housing magnetic resonance scanner 101. Signal processing system 109 may be partially or totally incorporated in a workstation that is structurally separate from and in communication with magnetic resonance scanner 101. Signal processing system 109 may be incorporated in a workstation that is structurally separate from and in communication with magnetic resonance scanner 101. Magnetic resonance signals received by signal processing system 109 may be associated with an magnetic resonance parameter, such as, for example, a relaxation time $T_1$, a relaxation time $T_2$, an apparent diffusion coefficient, a property associated with the blood oxygenation level dependent (BOLD) effect, a property associated with the diffusion tensor, etc.

Signal processing system 109 is in communication with data storage unit 108. By utilizing the database data on data storage unit 108, signal processing system 109 is capable of processing the magnetic resonance signals received from magnetic resonance scanner 101 to automatically identify a soft tissue substructure of interest in the magnetic resonance images showing a soft tissue region of subject 102. The results may be displayed on a viewing station 110 or a console station 111.

An operator 113 may manually enter regions of interest (ROIs) at input/output device 112. The ROIs may be embodied as binary masks, for example, with 1's encoding chosen pixels and 0's encoding pixels not chosen. The ROIs may encompass a soft tissue substructure in a soft tissue region being imaged and may be subsequently stored in data storage unit 108.

Figure 2A:
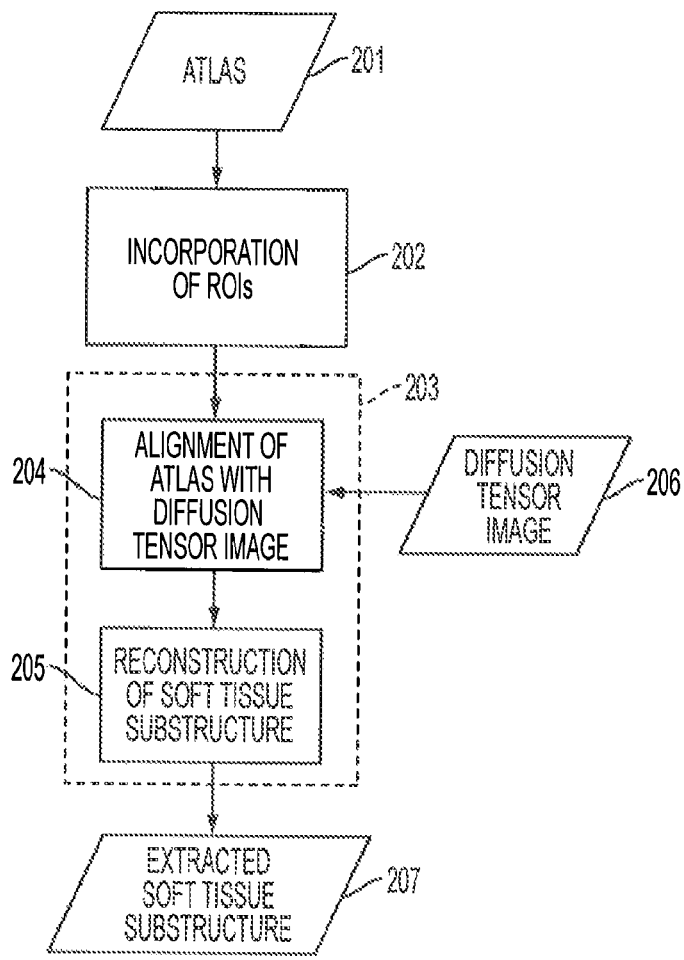
FIG. 2A shows a flow chart according to an embodiment of the current invention.

FIG. 2A shows a flow chart according to an embodiment of the current invention to extract soft tissue substructure of interest. Atlas 201 is a data set corresponding to a soft tissue region of a sub-population of humans. There are many ways to generate atlas 201. For example, atlas 201 may be a data set of magnetic resonance images of conventional magnetic resonance contrast (such as, $T_1$ weighted, $T_2$-weighed, proton-density weighted contrast) from a group of at least one human subject. Atlas 201 may also use diffusion tensor imaging (DTI)-derived images which show intra-white matter structures of sharper contrast. Examples of approaches to reveal such structures may include the use of color-coded orientation maps. For example, after the diagonalization of the diffusion tensor calculated from DTI data, one may obtain the principal eigenvector $\vec{v}_1$. A red, green, blue (RGB) value of 24-bit may then be assigned to the X, Y, and Z coordinates of $\vec{v}_1$. The RGB value may be subsequently used for display, for example, on a viewing station 110 or a console station 111, so that an operator may clearly identify white matter structures. It is also preferable to use an atlas representative of the population of interest. For example, if one is interested in neonatal brains, atlas 201 can be created by including multiple neonate brains. Thus, the term atlas is defined and shall be understood consistently within the confines of the specification.

Diffusion tensor image 206 may be calculated from a set of non-diffusion-weighted images (also known as $b_0$ images in the art) and diffusion-weighted images (DWIs). At least 6 DWIs may be needed to compute a tensor at a pixel. Typically, 12-90 DWIs with various diffusion encoding orientations may be used. A pixel-by-pixel tensor calculation may be applied to the combination of $b_0$ images and DWIs to yield a 3×3 diffusion tensor at each pixel. For a pixel-by-pixel tensor calculation, a multi-variate linear least-square fitting or a non-linear fitting may be used. For example, the diffusion tensor can be calculated using the following equation 1:

$$\ln\left[\frac{S}{S_0}\right] = -\int_0^{t'} \gamma^2 \left[\int_0^{t'} \overline{G(t'')} dt''\right] \cdot \overline{D} \cdot \left[\int_0^{t'} \overline{G(t'')} dt''\right] dt' \quad (1)$$

However, it is noted that the invention is applicable to any form of diffusion-weighted images with or without the above mentioned tensor calculation.

Block 202 is incorporation of regions of interest (ROIs) and may be accomplished by an experienced operator drawing ROIs that encompass a soft tissue substructure in the soft tissue being imaged. The ROIs may then be saved in data storage unit 108. The experienced operator may have extensive anatomical knowledge of a number of soft tissue substructures of interest including, for example, forceps major (FMa), forceps minor (FMi), anterior thalamic radiation (ATR), cingulum of the cingulated cortex (CgC), cingulum of the hippocampal region (CgH), corticospinal tract (CST), inferior fronto-occipital fasciculus (IFO), inferior longitudinal fasciculus (ILF), superior longitudinal fasciculus (SLF), the temporal projection of the SLF (tSLF), uncinate fasciculus (UNC), etc. of the brain white matter. For example, multiple regions-of-interest (ROIs) that define a specific brain region may be placed. This process requires precise anatomical knowledge on the operator. Currently, a knowledgeable operator may not be available for many hospitals or clinics, which may hamper wide application of diffusion tensor imaging in research and clinical studies.

The stored ROIs may then be used in processing diffusion tensor image 206 to generate extracted soft tissue substructure 207 by block 203. Block 203 starts with block 204 that aligns the atlas and the incorporated ROIs with diffusion tensor image 206 and proceeds to block 205 that reconstructs soft tissue substructures defined by the ROIs. In block 204, the alignment is to make the shape, size, and/or orientation of the atlas 201 similar to that of the diffusion tensor image 206. The alignment may be performed by using one of existing transformation methods such as, for example, a 6-mode linear transformation, a 12-mode affine transformation, a non-linear transformation that may increase the accuracy of the transformation, etc. The transformation may be warping atlas 201 to diffusion tensor image 206 or warping diffusion tensor image 206 to atlas 201. In block 205, a soft tissue substructure in the soft tissue region shown in diffusion tensor image 206 may be reconstructed. The soft tissue substructure may be, for example, a fiber tract in brain white matter, a region in brain white matter, a muscle fiber, a myocardial fiber, etc. For example, tractography may be performed and fiber tracts that satisfy the locations and conditions of the incorporated ROIs are extracted. An example of a tractography method that may be used in an embodiment of the current invention is the method of Fiber Assignment by Continuous Tracking (FACT) (Mori, S., Crain, B. J., Chacko, V. P., van Zijl, P. C. M., 1999. Three dimensional tracking of axonal projections in the brain by magnetic resonance imaging. Annal. Neurol. 45, 265-269;

Xue, R., van Zijl, P. C. M., Crain, B. J., Solaiyappan, M., Mori, S., 1999. In vivo three-dimensional reconstruction of rat brain axonal projections by diffusion tensor imaging. Magn. Reson. Med 42, 1123-1127). Examples of tractography in some embodiments of the current invention may be used to generate results regarding such properties as, for example, tensor trace, fiber anisotropy, fiber orientation, etc.

Figure 2B:
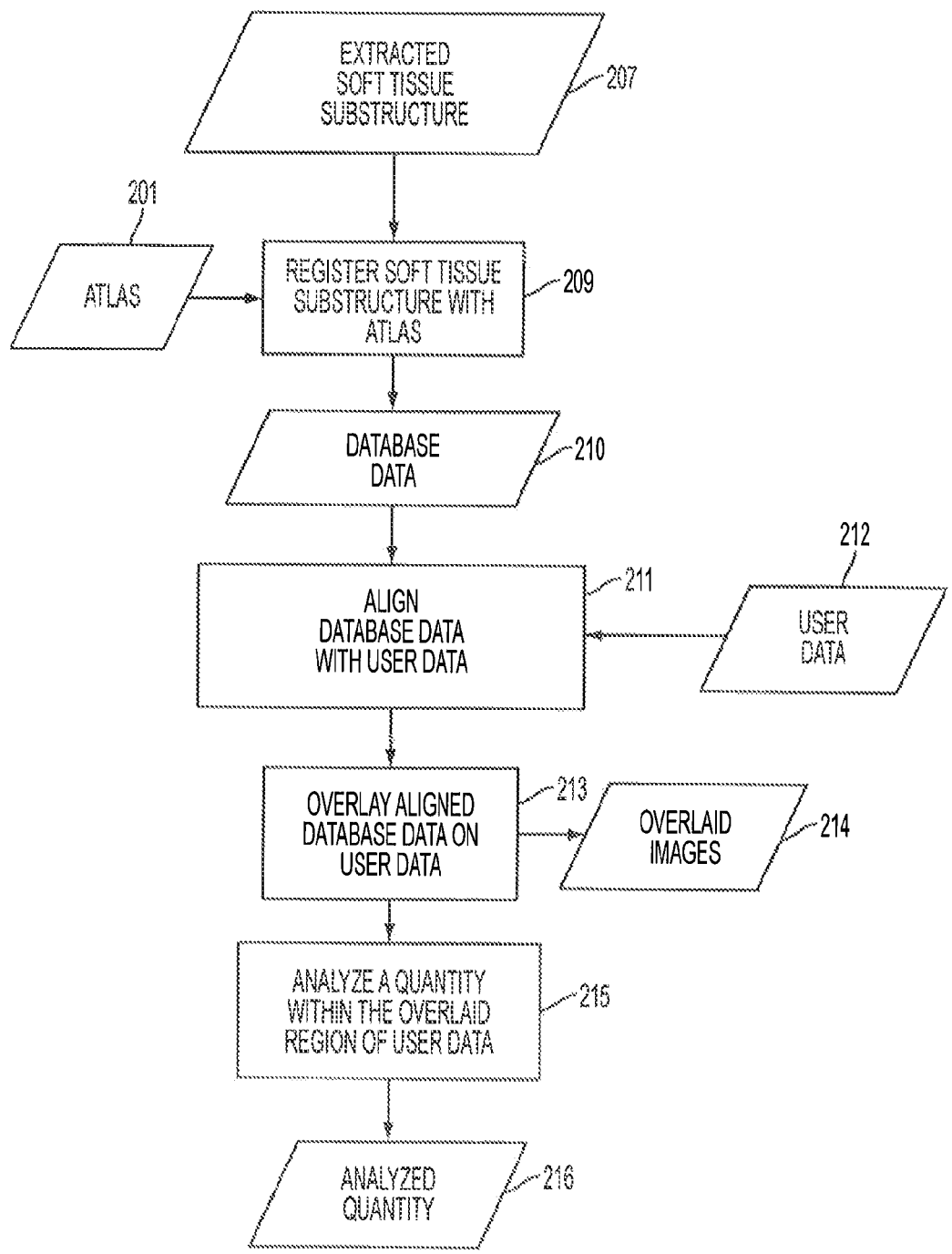
FIG. 2B shows a flow chart according to an embodiment of the current invention.

FIG. 2B shows a flow chart according to an embodiment of the current invention. Extracted soft tissue substructures 207 may be processed by block 209 to be spatially registered with atlas 201. For example, a number of extracted soft tissue substructures from multiple human subjects may be used. For example, the spatial coordinates of extracted soft tissue substructure 207 may be registered to atlas 201 by transforming the shape, size, and/or orientation of the diffusion tensor image from which soft tissue substructure 207 was extracted to that of atlas 201. The role of the transformation is to align atlas 201 with that of the diffusion tensor image from which soft tissue substructure 207 was extracted. The alignment can be in terms of spatial orientation as well as shape, size, orientation etc. The alignment may be achieved by using one of existing transformation methods such as, for example, a 6-mode linear transformation, a 12-mode affine transformation, a non-linear transformation that may increase the accuracy of the transformation, etc. The transformation may be warping atlas 201 to extracted soft tissue substructure 207 or warping extracted soft tissue substructure 207 to atlas 201. The registration process produces database data 210. If extracted soft tissue substructure data from more than one subject is being registered to produce database data 210, then a probabilistic map may become feasible. For example, the extracted soft tissue substructure data from each subject can be binalized, in which the pixels that contain the tract receive a scalar value "1" and all other pixels receive "0." The X, Y, and Z coordinates of binalized and extracted soft tissue substructure data from each subject may be registered with atlas 201 to produce database data 210. For example, if the X, Y, and Z coordinates of soft tissue substructure data from ten subjects are being registered with the atlas to produce database data 210, then there would be pixels, in database data 210, with the number 10, 9, 8, 7, 6, 5, 4, 3, 2, 1, and 0. When divided by 10, each pixel obtains a number ranging 0-1, which encodes the probability to have this specific soft tissue substructure at the pixel location.

In block 211, database data 210 may be aligned with user data 212. User data 212 may be, for example, a magnetic resonance image of a subject showing the same soft tissue region as that of database data 210. Images from other modalities, such as computed tomography (CT), positron emission tomography (PET), etc., may also form user data 212. The alignment may be achieved by using one of existing transformation methods such as, for example, a 6-mode linear transformation, a 12-mode affine transformation, a non-linear transformation that may increase the accuracy of the transformation, etc. The alignment is to transform the shape, size, and/or orientation of database data 210 to user data 212. The transformation may be warping database 210 to user data 212 or warping user data 212 to database data 210. Once aligned, information in database data 210 that identifies a specific soft tissue substructure may be overlaid on user data 212, as shown in block 213. The result of block 213 may be displayed as, for example, an overlaid image 214. Overlaid image 214 may be showing the overlaid region in, for example, a pseudo-color map, for visualization. Block 215 may analyze a quantity within the overlaid region of user data 214. Analyzed quantity 216 may be indicative of a physiologic condition of the subject being analyzed. Analyzed quantity 216 may be, for example, pixel intensity, relaxation time $T_1$, relaxation time $T_2$, apparent diffusion coefficient, a quantity associated with the diffusion tensor, a quantity associated with the blood oxygenation level dependent (BOLD) effect, etc.

Figure 2C:
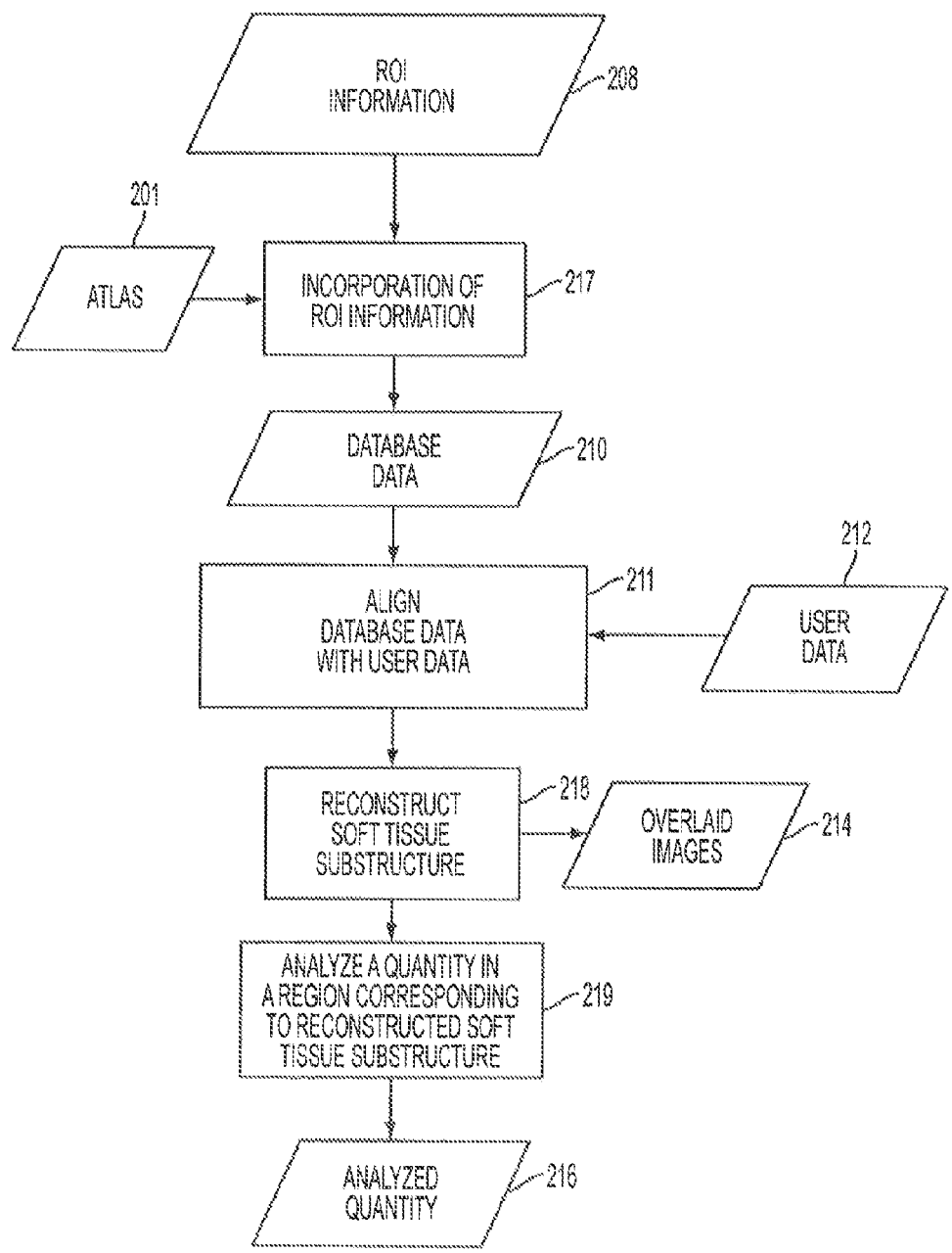
FIG. 2C shows a flow chart according to an embodiment of the current invention.

FIG. 2C shows a flow chart according to an embodiment of the current invention. ROI information 208 may be processed by block 217 to be incorporated with atlas 201 to generate database data 210. For example, a number of ROIs encompassing a soft tissue substructure in a soft tissue region may be used.

In block 211, database data 210 may be aligned with user data 212. User data 212 may be, for example, diffusion tensor imaging data of a subject showing the same soft tissue region as that of database data 210. The alignment may be achieved by using one of existing transformation methods such as, for example, a 6-mode linear transformation, a 12-mode affine transformation, a non-linear transformation that may increase the accuracy of the transformation, etc. The alignment is to transform the shape, size, and/or orientation of database data 210 to user data 212. The transformation may be warping database 210 to user data 212 or warping user data 212 to database data 210. Once aligned, user data 212 may be reconstructed to reveal a specific soft tissue substructure defined by the ROI information 208. For example, user data 212 may be diffusion tensor imaging data having both $b_0$ images with no diffusion weighting and DWI images with various diffusion weightings. The soft tissue substructure may be, for example, a fiber tract in brain white matter, a region in brain white matter, a muscle fiber, a myocardial fiber, etc. Exemplary reconstruction may be a tractography method, for example, the method of Fiber Assignment by Continuous Tracking (FACT), that may generate results regarding such properties as, for example, tensor trace, fiber anisotropy, fiber orientation, etc. The result of block 218 may be displayed as, for example, an overlaid image 214. Overlaid image 214 may be showing the overlaid region in, for example, a pseudo-color map, for visualization. For example, reconstructed soft tissue substructure may be overload on the $b_0$ images in a pseudo-color map. Block 215 may analyze a quantity within the overlaid region of user data 214. Analyzed quantity 216 may be indicative of a physiologic condition of the subject being analyzed. Analyzed quantity 216 may be, for example, pixel intensity, relaxation time $T_1$, relaxation time $T_2$, apparent diffusion coefficient, a quantity associated with the diffusion tensor, a quantity associated with the blood oxygenation level dependent (BOLD) effect, etc.

To demonstrate some embodiments of the current invention, a number of experiments were conducted on a 1.5T magnetic resonance (MR) scanner (Gyroscan NT, Philips Medical Systems). Diffusion Tensor Imaging (DTI) data were acquired with a single-shot, echo-planar imaging (EPI) sequence with sensitivity encoding (SENSE) (Pruessmann et al., 1999 SENSE: sensitivity encoding for fast MRI. Magn Reson Med 42, 952-962), using a parallel-imaging factor of 2.5. The imaging matrix was 96×96 with a field-of-view of 240×240 mm (nominal resolution, 2.5 mm), zero-filled to 256×256 pixels. Transverse sections of 2.5 mm thickness were acquired parallel to the anterior commissure-posterior commissure line. A total of 50-55 sections covered the entire hemisphere and brainstem without gaps. The echo time (TE) and repetition time (TR) were 80 ms and >8,000 ms, respectively. Diffusion weighting was encoded along 30 independent orientations and the b-value was 700 s/mm². Five additional images with minimal diffusion weighting (b≈33 s/mm²) were also acquired. The scanning time per DTI dataset was approximately 6 minutes. To enhance the signal-to-noise ratio, imaging was repeated three times.

The acquired DTI datasets were transferred to a personal computer running a Windows platform and were processed using DtiStudio, an DTI data processing software. Images were first processed to remove small bulk motion that may have occurred during the scans. During tensor calculation, the six elements of the diffusion tensor were calculated for each pixel using multivariate linear fitting. After diagonalization, three eigenvalues and corresponding eigenvectors were obtained. The eigenvector associated with the largest eigenvalue was used as an indicator of the fiber orientation. Fractional anisotropy (FA) (Pierpaoli and Basser, 1996. Toward a quantitative assessment of diffusion anisotropy. Magn. Reson. Med. 36, 893-906.) was used. We also created an averaged diffusion-weighted image (aDWI) by adding all of the diffusion-weighted images. This image was used for image registration purposes.

Figure 3A:
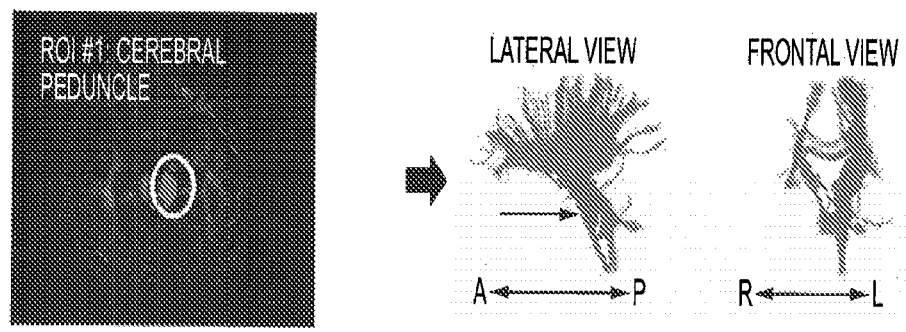
FIGS. 3A-3D show example applications of regions of interest (ROIs) for the reconstruction of the corticospinal tract (CST) and demonstration of anatomical constraints posed by each ROI.
Figure 3B:
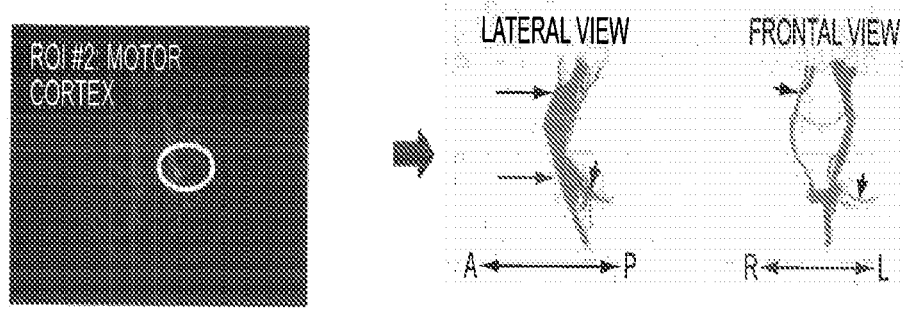
Figure 3C:
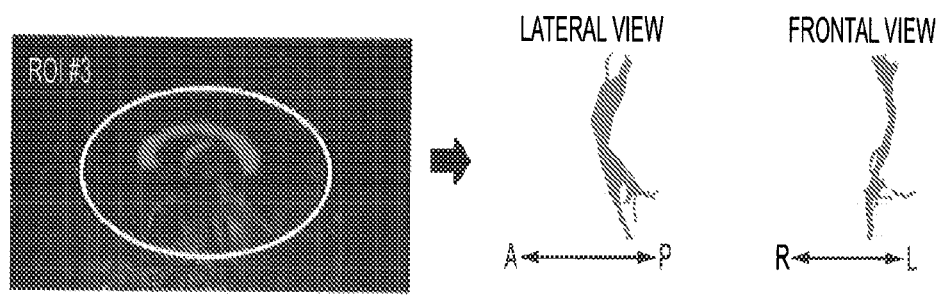
Figure 3D:
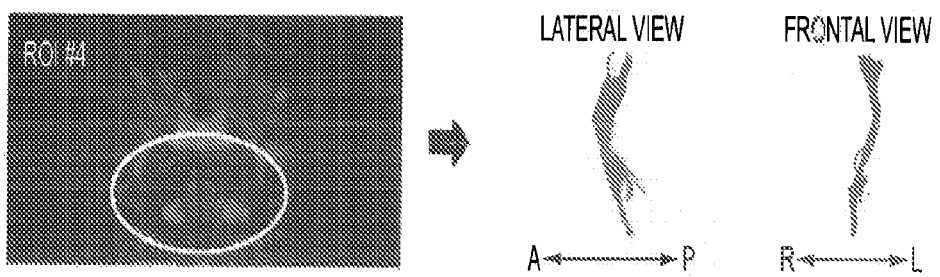

FIG. 3A-3D show examples of applications of ROIs for reconstruction of the corticospinal tract (CST) and demonstration of anatomical constraints posed by each ROI. In FIG. 3A, ROI #1 defines the entire left midbrain and leads to the extraction of a large amount of projection fibers that connect the cortex and the brainstem. In FIG. 3B, ROI #2 defines the pre-central white matter region and the logic combination of ROI #1 and ROI #2 drastically increases the specificity of the reconstruction results for the CST. It is noted that each ROI is large and its placement is not precisely targeted to the exact contour of CST. However, the anatomical constraints posed by multiple ROIs are strong enough to select only a small number of tracts. Furthermore, ROIs can be placed to remove all tracts that penetrate them (called a "NOT" ROI). For example, placement of ROI #3 in FIG. 3C removes tracts that penetrate the midline and placement of ROI#4 in FIG. 3D removes projections to the cerebellum (indicated by orange arrows). It is noted that A, P, R, and L in FIGS. 3A-3D indicate anterior, posterior, right, and left orientations.

It is noted that the logic functions of the ROIs can be adapted to the particular application. For example, ROI #1 in FIG. 3A operates as "OR", which means all tracts that penetrate ROI #1 will be retrieved. Meanwhile, ROI #2 operates as "AND", which means only tracts that penetrate ROI #1 and #2 are retrieved. ROI #3 and ROI #4 operate as "NOT", which means all tracts that penetrate these ROIs are removed.

The ROIs were transferred to the international consortium of brain mapping (ICBM)-DTI-81 atlas manually to form database data 210. Database data 210 included multiple ROIs for one image slice. Some ROIs were combined by an "AND" operation; thus tracts that penetrate these ROIs were selected for reconstruction. Some ROIs were for a "NOT" operation that can remove commonly found contaminations. The database data 210 was then transferred to data from a new subject using an affine transformation and tracking was performed automatically. A linear transformation based on an Automated Image Registration (AIR) algorithm (Woods et al., 1998. Automated image registration: I. General methods and intrasubject, intramodality validation. J Comput Assist Tomogr 22, 139-152.) was used. To drive the transformation, aDWI images from database data 210 and the new subject were used. The transformation of DTI data from the new subject was read by DtiStudio to perform the automated reconstruction. The final display may apply a threshold value to prune pixels having insignificant reconstructed intensity.

To evaluate the accuracy of the automated tracking results, the tracts were manually reconstructed by an experienced rater. The spatial matching was examined using a kappa analysis (Landis and Koch, 1977. The measurement of observer agreement for categorical data. Biometrics 33, 159-174). The automated and manual tracking results were first converted to binary information of the same pixel dimension as the DTI data (256×256×50-55), in which pixels that were occupied by the tracts were assigned a value of 1, and other non-occupied pixels were assigned a value of 0. Two tracking results were then superimposed, which yielded four different pixel categories: (1) pixels did not contain the tract in either trial (nn); (2) pixels that contained the tract in only one of the two trials (pn, np); and (3) pixels that contained the tracts in both trials (pp). Expectation values (Enn, Enp, Epn, and Epp) for each class were then calculated using the following equations:

$$\text{Expected } nn(Enn)=(nn+np)(nn+pn)/N \quad (2)$$

$$\text{Expected } np(Enp) \text{ or } Epn=(nn+np)(np+pp)/N \text{ or}(nn+pn)(pn+pp)/N \quad (3)$$

$$\text{Expected } pp(Epp)=(pn+pp)(np+pp)/N \quad (4)$$

where N=nn+np+pn+pp is the total number of pixels of the white matter in each subject. For the calculation, pixels with an FA lower than the threshold (FA>0.2) were not included. Then ιc (kappa) was calculated by $$\kappa=(\text{observed agreement}-\text{expected agreement})/(100-\text{expected agreement}) \quad (5)$$

where observed agreement=(nn+pp)/N×100 and expected agreement=(Enn+Epp)/N×100. The analysis was applied in a pair-wise manner; there are three combinations from the three trials. The κ values were determined for the three pair-wise combinations and an average κ was determined from the 10 normal subjects. According to criteria set by Landis and Koch, the κ value of 0.11-0.2 is considered "slight," 0.21-0.4 is "fair," 0.41-0.60 is "moderate," 0.61-0.80 is "substantial," and 0.81-1.0 is "almost perfect" agreement.

Table 1 summarizes agreement of the manual and automated methods for 10 normal subjects. Kappa values more than 0.80 (almost perfect) were found for all 11 tracts, indicating a high level of matching. The lowest kappa of 0.81+/− 0.07 was found for the CST. Thus, we conclude the quality of automatic reconstruction based on the invention is satisfactory.

TABLE 1

Agreement between manual and automated methods measured in 10 healthy volunteers

| | Tract Name | | | | | |
|---|---|---|---|---|---|---|
| | ATR | CG_C | CG_H | CST | FORCEPS Major | FORCEPS Minor |
| Average | 0.89 ± 0.05* | 0.87 ± 0.07 | 0.92 ± 0.05 | 0.81 ± 0.07 | 0.91 ± 0.07 | 0.93 ± 0.06 |

TABLE 1-continued

Agreement between manual and automated methods measured in 10 healthy volunteers

| | Tract Name | | | | |
|---|---|---|---|---|---|
| | IFO | ILF | SLF | SLF_temporal | UNC |
| Average | 0.90 ± 0.06 | 0.89 ± 0.08 | 0.87 ± 0.08 | 0.95 ± 0.06 | 0.96 ± 0.03 |

*Average of kappa values and standard deviations

The ROIs may be applied to, for example, diffusion tensor imaging data to perform tractography that extracts a fiber tract satisfying the locations and conditions of the ROIs. The extracted fiber tract from a group of at least one human subject may be used to register with an atlas of the human brain, thereby generating, for example, a probabilistic map showing the probability of the fiber tract spatially.

Figure 4B:
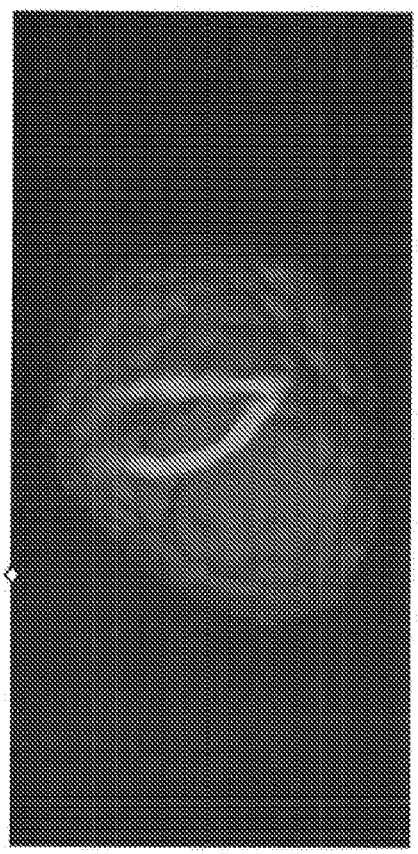
FIG. 4B shows an example of a probabilistic map of the CST in 3-dimension (3D). The 3D probability map is overlaid with a 3D representation of the brain and the gray scale represents probability.
Figure 4A:
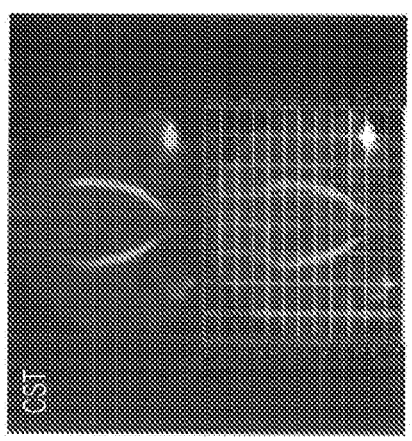
FIG. 4A shows an example of a probabilistic map of the corticospinal tract (CST) in Talairach coordinates. The probability map is overlaid with Talairach grid and the gray scale represents probability.

FIG. 4A shows an example of a probabilistic map of the corticospinal tract (CST) in Talairach coordinates. The 3D probability map is overlaid with Talairach grid and the gray scale represents probability.

FIG. 4B shows an example of a probabilistic map of the CST in 3-dimension (3D). The 3D probability map is overlaid with a 3D representation of the brain and the gray scale represents probability.

Figure 4E:
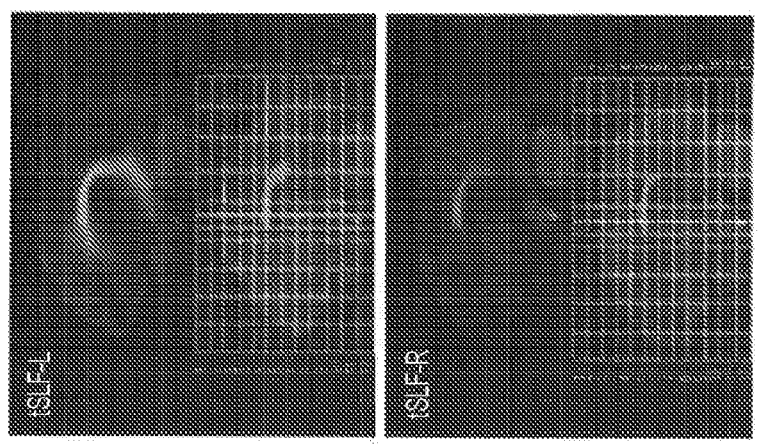
FIG. 4E shows examples of probabilistic maps of both the temporal projection of the Superior Longitudinal Fasciculus left (tSLF-L) and the temporal projection of the Superior Longitudinal Fasciculus right (tSLF-R) in Talairach coordinates. The probability maps are overlaid with Talairach grid and the gray scale represents probability.
Figure 4D:
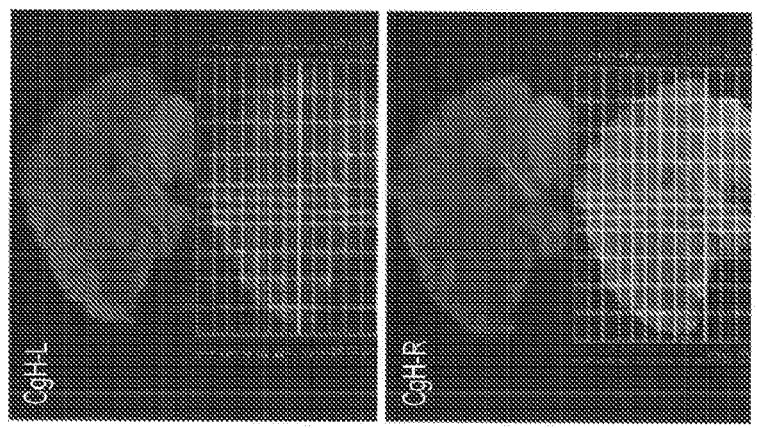
FIG. 4D shows examples of probabilistic maps of both the cingulum of the hippocampal region left (CgH-L) and the cingulum of the hippocampal region right (CgH-R) in Talairach coordinates. The probability maps are overlaid with Talairach grid and the gray scale represents probability.
Figure 4C:
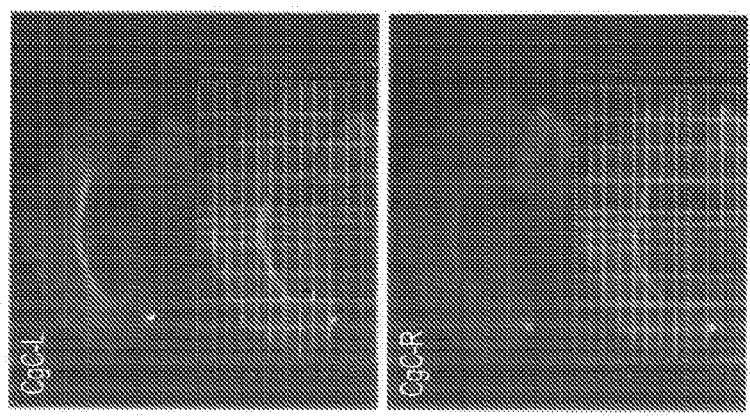
FIG. 4C shows examples of probabilistic maps of both the cingulated cortex left (CgC-L) and cingulated cortex right (CgC-R) in Talairach coordinates. The probability maps are overlaid with Talairach grid and the gray scale represents probability.

FIG. 4C shows examples of probabilistic maps of both the cingulated cortex left (CgC-L) and cingulated cortex right (CgC-R) in Talairach coordinates. The 3D probability maps are overlaid with Talairach grid and the gray scale represents probability.

FIG. 4D shows examples of probabilistic maps of both the cingulum of the hippocampal region left (CgH-L) and the cingulum of the hippocampal region right (CgH-R) in Talairach coordinates. The 3D probability maps are overlaid with Talairach grid and the gray scale represents probability.

FIG. 4E shows examples of probabilistic maps of both the temporal projection of the Superior Longitudinal Fasciculus left (tSLF-L) and the temporal projection of the Superior Longitudinal Fasciculus right (tSLF-R) in Talairach coordinates. The 3D probability maps are overlaid with Talairach grid and the gray scale represents probability.

Figure 4H:
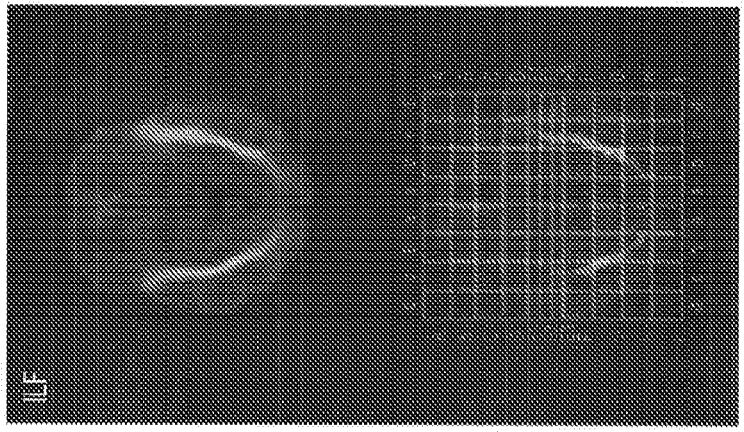
FIG. 4H shows an example of a probabilistic map of the inferior longitudinal fasciculus (ILF) in Talairach coordinates. The probability map is overlaid with Talairach grid and the gray scale represents probability.
Figure 4G:
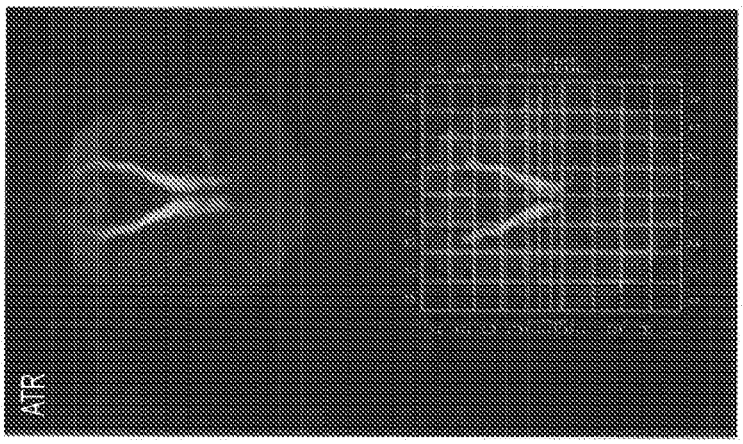
FIG. 4G shows an example of a probabilistic map of the anterior thalamic radiation (ATR) in Talairach coordinates. The probability map is overlaid with Talairach grid and the gray scale represents probability.
Figure 4F:
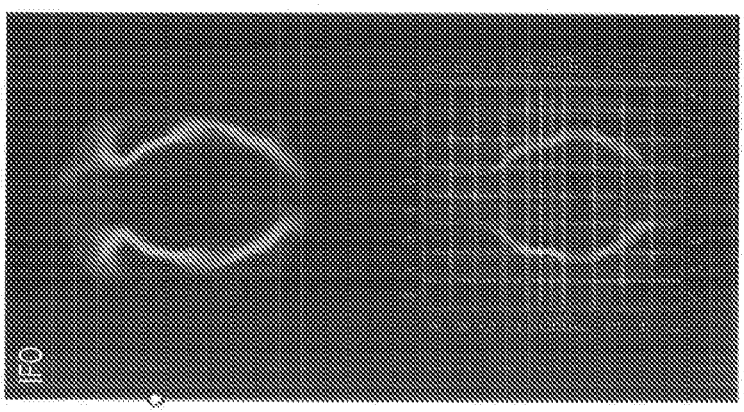
FIG. 4F shows an example of a probabilistic map of the inferior fronto-occipital facsiculus (IFO) in Talairach coordinates. The probability map is overlaid with Talairach grid and the gray scale represents probability.

FIG. 4F shows an example of a probabilistic map of the inferior fronto-occipital facsiculus (IFO) in Talairach coordinates. The 3D probability map is overlaid with Talairach grid and the gray scale represents probability.

FIG. 4G shows an example of a probabilistic map of the anterior thalamic radiation (ATR) in Talairach coordinates. The 3D probability map is overlaid with Talairach grid and the gray scale represents probability.

FIG. 4H shows an example of a probabilistic map of the inferior longitudinal fasciculus (ILF) in Talairach coordinates. The 3D probability map is overlaid with Talairach grid and the gray scale represents probability.

Figure 4K:
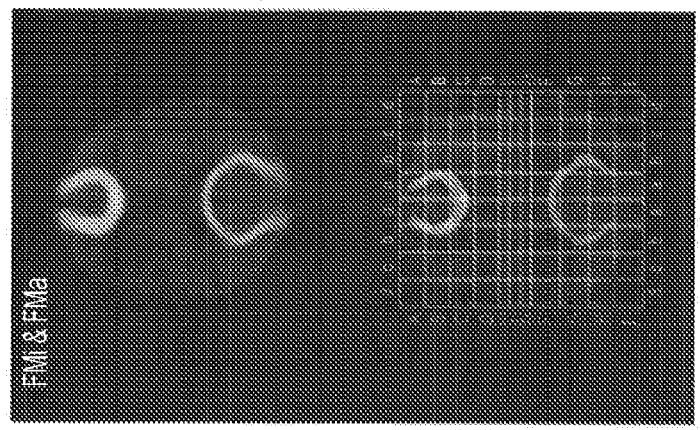
FIG. 4K shows examples of probabilistic maps of both the forceps minor (FMi) and forceps major (FMa) in Talairach coordinates. The probability maps are overlaid with Talairach grid and the gray scale represents probability.
Figure 4J:
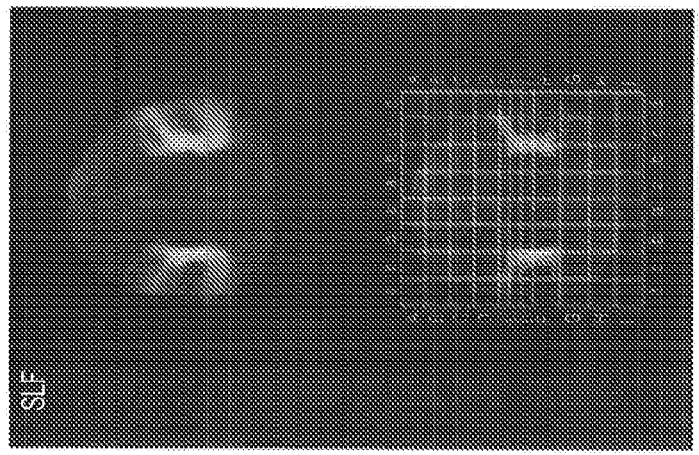
FIG. 4J shows an example of a probabilistic map of the SLF in Talairach coordinates. The probability map is overlaid with Talairach grid and the gray scale represents probability.
Figure 4I:
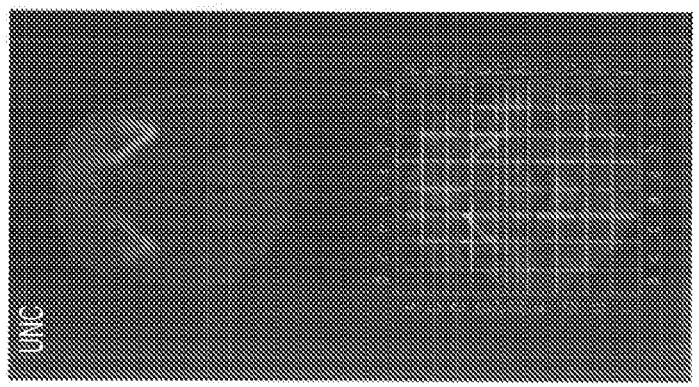
FIG. 4I shows an example of a probabilistic map of the uncinate fasciculus (UNC) in Talairach coordinates. The probability map is overlaid with Talairach grid and the gray scale represents probability.

FIG. 4I shows an example of a probabilistic map of the uncinate fasciculus (UNC) in Talairach coordinates. The 3D probability map is overlaid with Talairach grid and the gray scale represents probability.

FIG. 4J shows an example of a probabilistic map of the SLF in Talairach coordinates. The 3D probability map is overlaid with Talairach grid and the gray scale represents probability.

FIG. 4K shows examples of probabilistic maps of both the forceps minor (FMi) and forceps major (FMa) in Talairach coordinates. The 3D probability maps are overlaid with Talairach grid and the gray scale represents probability.

The probabilistic maps of fiber tracts may also be incorporated in database data 210 as information identifying the locations of the fiber tracts. The identifying information may be aligned with user data 212. The alignment can be in terms of spatial orientation as well as shape, size, orientation etc. The alignment may be achieved by using one of existing transformation methods such as, for example, a 6-mode linear transformation, a 12-mode affine transformation, a non-linear transformation that may increase the accuracy of the transformation, etc. The alignment is to transform the shape, size, and/or orientation of the probabilistic maps to that of user data 212. The transformation may be warping the probabilistic maps to user data 212 or warping user data 212 to the probabilistic maps. The aligned identifying information may be overlaid on user data 212. Pixels with insignificant values, for example, within a threshold value of the identifying information, may be pruned.

The identifying information may be visualized as an overlay image. For example, the identifying information may be overlaid on a magnetic resonance image in a pseudo-color map. FIGS. 5A-5D show exemplary overlays of an exemplary probabilistic map of the CST on $T_2$-weighted images of a multiple sclerosis (MS) patient in the Montreal Neurological Institute (MNI) coordinate. $T_2$-weighted images are shown on a gray scale while the probabilistic maps identifying locations of the CST are shown on a pseudo-color map. The images are at Z=60 mm, Z=80 mm, Z=100 mm, and Z=120 for FIGS. 5A-5D respectively.

The overlaid spatial information enables various types of image evaluation, which are otherwise impossible. For example, if there is a $T_2$-hyperintensity lesion in the white matter of a patient, we could only report "there is a $T_2$-hyperintensity lesion in the white matter". However, the overlaid spatial information of a fiber tract allows us to elaborate the report. For example, we may report "there is a $T_2$-hyperintensity on the CST as shown in FIGS. 5A-5D."

Figure 6A:
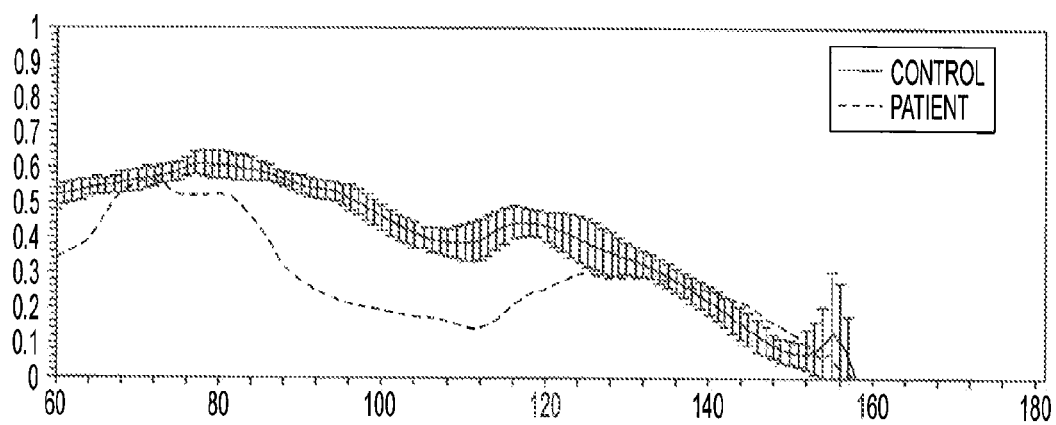
FIGS. 6A-6B show examples of results of quantifying an MR parameter of fractional anisotropy along the CST.
Figure 6B:
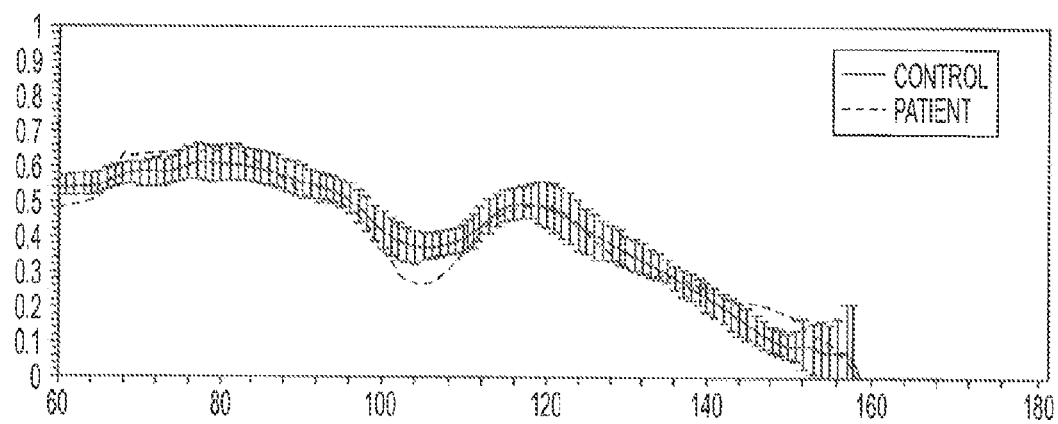

It is also possible to quantify an MR parameter along the locations of an identified tract to evaluate, for example, how a lesion propagates along the tract. The MR parameter may be, for example, a relaxation time $T_1$, a relaxation time $T_2$, a property associated with the diffusion tensor, a property associated with the blood oxygenation level dependent (BOLD) effect, etc. FIGS. 6A-6B show exemplary quantifications of the fractional anisotropy (FA), associated with the diffusion tensor, along the identified CST left (CSTL) and CST right (CSTR) tract, respectively, from various subjects. The red line represents average and standard deviation of the FA values from control human subjects with normal brains. The blue line shows FA values of one MS patient over the same tract. The abnormality in FA values along the CSTL tract is clearly shown for the MS patient. Thus, the analyzed FA values may be used for differentiation and localization purposes in the diagnosis of MS condition or monitoring of drug therapy.

Figure 7A:
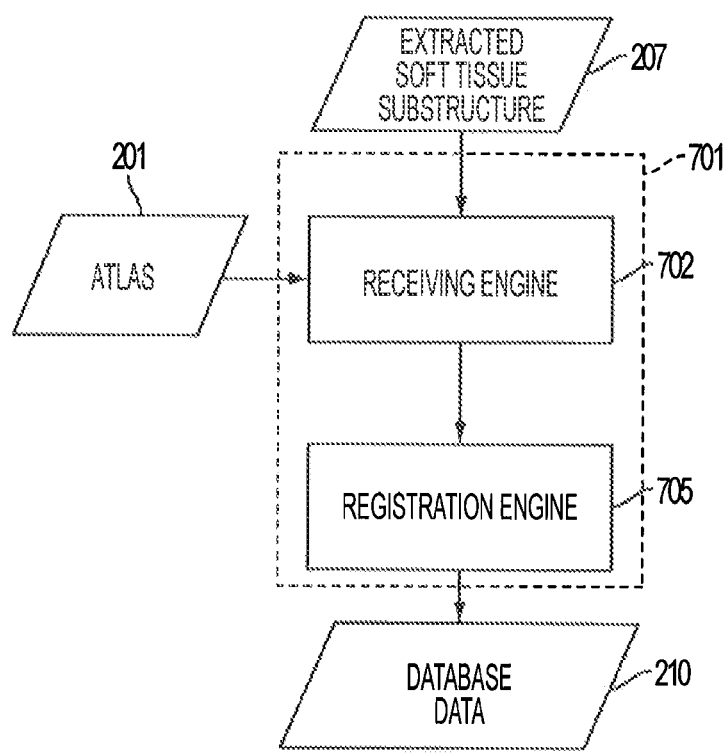
FIG. 7A shows a schematic illustration according to an embodiment of the invention.

FIG. 7A shows a schematic illustration according to an embodiment of the current invention. A workstation 701 may comprise a receiving engine 702 to receive atlas 201 and processed data encoding extracted soft tissue substructure 207, a registration engine 705 to align extracted soft tissue substructure 207 with atlas 201 and generate database data 210 including information identifying the extracted soft tissue substructure 207. Receiving engine 702 may be a peripheral device, a computer, or a computer system configured to receive atlas 201. Registration engine 705 may be a programmed computer or computer system, including an embedded component such as, for example, a digital signal processing (DSP) chip and/or field programmable gated array (FPGA). It is noted that these are not limiting examples. For example, the spatial coordinates of extracted soft tissue substructure 207 may be registered with atlas 201 by aligning the shape, size, and/or orientation of the diffusion tensor image from which soft tissue substructure 207 was extracted to that of atlas 201. The alignment may be achieved by using one of existing transformation methods such as, for example, a 6-mode linear transformation, a 12-mode affine transformation, a non-linear transformation that may increase the accuracy of the transformation, etc. If there are extracted soft tissue substructure data from more than one subject, then a probabilistic map may become feasible to be included in database data 210 to encode the spatial probability of a specific soft tissue substructure.

Generated database data 210 may be stored, for example, on a data storage unit 108. Generated database data 210 may also be stored, for example, on a computer-readable medium. Examples of computer readable mediums may include a hard disk drive; a floppy disk; a magneto-optical disk; an optical disk; a magnetic tape; a flash removable memory; and a memory chip.

Figure 7B:
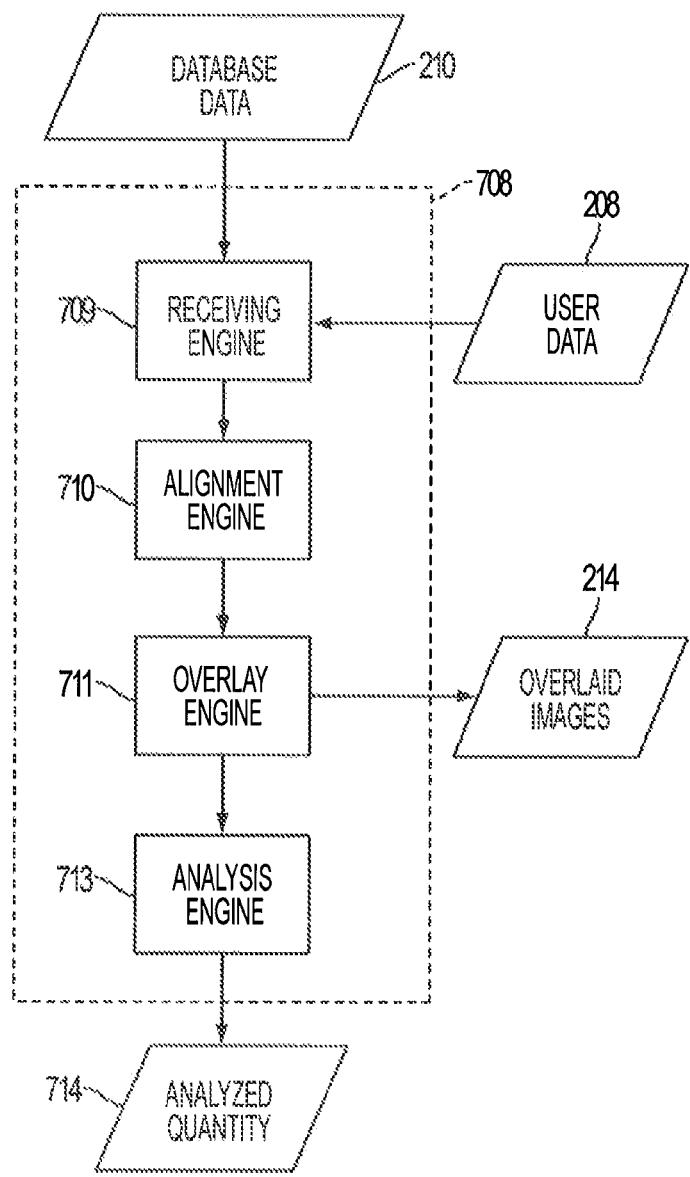
FIG. 7B shows a schematic illustration according to an embodiment of the invention.

FIG. 7B shows a schematic illustration according to an embodiment of the current invention. Workstation 715 receives database data 210 and user data 208 and generates an overlaid image 214 or an analyzed quantity 714. User data 208 may be, for example, a magnetic resonance image from a human subject showing a soft tissue region. Workstation 708 comprises a receiving engine 709 to receive database data 210 and user data 208, an alignment engine 710 to align database data 210 with user data 208, an overlay engine 711 to overlay information in database data 210 that identifies soft tissue substructures in the soft tissue region of user data 208, and an analysis engine 713 to analyze, within an area being overlaid on user data 208, a quantity indicative of a physiologic condition of interest. Receiving engine 709 may be a peripheral device, a computer, or a computer system configured to receive database data 210 and user data 208. Alignment engine 710 may use one of the existing transformation methods such as, for example, a 6-mode linear transformation, a 12-mode affine transformation, a non-linear transformation that may increase the accuracy of the transformation, etc. Overlay engine 711 may output an overlaid image showing the information from the database data 210 that identifies, for example, a specific soft tissue substructure on user data 208. Analysis engine 713 may output analyzed quantity 714 indicative of a physiological condition within an area being overlaid on user data 208. Alignment engine 710, overlay engine 711, and analysis engine 713 may be a programmed computer or computer system, including an embedded component such as, for example, a digital signal processing (DSP) chip, a graphics processing unit (GPU) chip, and/or a field programmable gated array (FPGA). It is noted that these are not limiting examples.

Figure 7C:
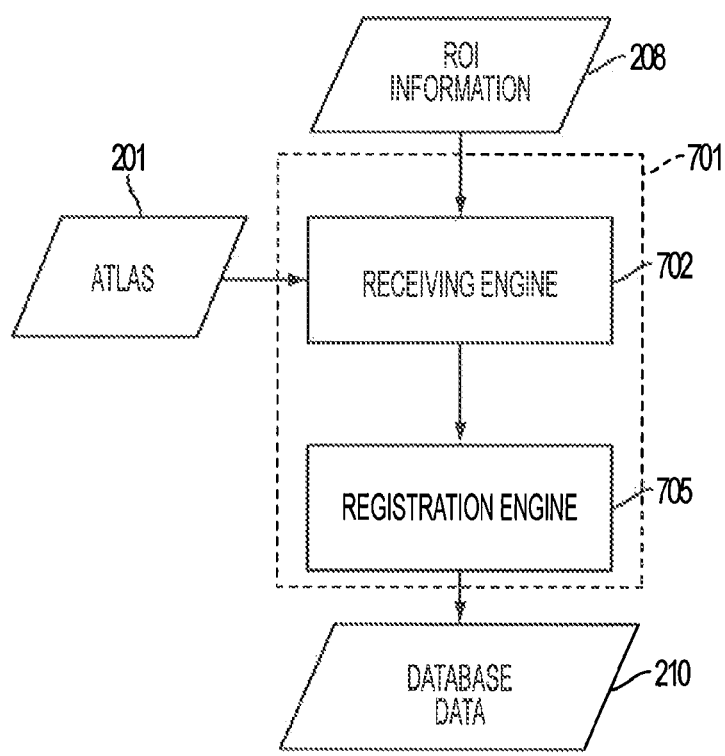
FIG. 7C shows a schematic illustration according to an embodiment of the invention.

FIG. 7C shows a schematic illustration according to an embodiment of the current invention. A workstation 701 comprising a receiving engine 702 to receive atlas data 201 and ROI information 208 corresponding to at least one soft tissue substructure of interest, a registration engine 705 to align ROI information 702 with atlas 201 and generate database data 210 including information identifying the soft tissue substructure of interest. Receiving engine 702 may be a peripheral device, a computer, or a computer system configured to receive atlas 201. Registration engine 705 may be a programmed computer or computer system, including an embedded component such as, for example, a digital signal processing (DSP) chip and/or field programmable gated array (FPGA). It is noted that these are not limiting examples. For example, multiple ROIs for one image slice may constitute ROI information 208. For each, soft tissue substructure reconstructed from the multiple ROIs at one image slice may be combined in a digital logic manner to generate the reconstructed soft tissue substructure. For example, ROI information 208 may be registered with atlas 201 by aligning ROI information to atlas 201. The alignment may be achieved by using one of existing transformation methods such as, for example, a 6-mode linear transformation, a 12-mode affine transformation, a non-linear transformation that may increase the accuracy of the transformation, etc.

Generated database data 210 may be stored, for example, on a data storage unit 108. Generated database data 210 may also be stored, for example, on a computer-readable medium. Examples of computer readable mediums may include a hard disk drive; a floppy disk; a magneto-optical disk; an optical disk; a magnetic tape; a flash removable memory; and a memory chip.

Figure 7D:
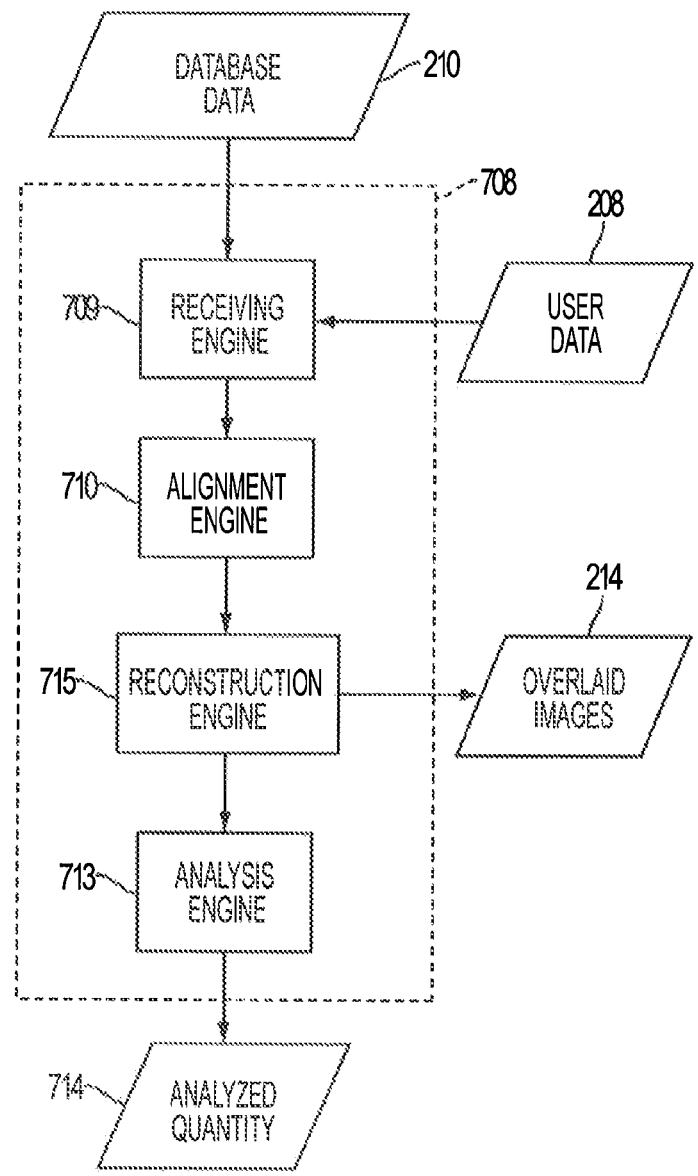
FIG. 7D shows a schematic illustration according to an embodiment of the invention.

FIG. 7D shows a schematic illustration according to an embodiment of the current invention. Workstation 715 receives database data 210 and user data 208 and generates an overlaid image 214 or an analyzed quantity 714. User data 208 may be, for example, diffusion tensor imaging (DTI) data from a human subject corresponding to a soft tissue region. Workstation 708 comprises a receiving engine 709 to receive database data 210 and user data 208, an alignment engine to align database data 210 with user data 208, a reconstruction engine 715 to reconstruct soft tissue substructures in user data 208 identified by the information in database data, and an analysis engine to analyze a quantity indicative of a physiologic condition of interest within an area covered by the reconstructed soft tissue substructure. Receiving engine 709 may be a peripheral device, a computer, or a computer system configured to receive database data 210 and user data 208. Alignment engine 710 may use one of the existing transformation methods such as, for example, a 6-mode linear transformation, a 12-mode affine transformation, a non-linear transformation that may increase the accuracy of the transformation, etc. Reconstruction engine 715 may output an overlaid image showing the reconstructed soft tissue substructure on user data 208. Analysis engine 713 may output analyzed quantity 714 indicative of a physiological condition within an area on user data 208 covered by the reconstructed soft tissue substructure. Alignment engine 710, reconstruction engine 715, and analysis engine 713 may be a programmed computer or computer system, including an embedded component such as, for example, a digital signal processing (DSP) chip, a graphics processing unit (GPU) chip, and/or a field programmable gated array (FPGA). It is noted that these are not limiting examples.

Workstations 701 and 708 may be a computer with at least one central processing unit (CPU) and a plurality of memory. Workstations 701 and 708 may also be a dedicated processing machine with such devices as, for example, field programmable gated array (FPGA), digital signal processing (DSP), application specific integrated circuit (ASIC), etc. that realize the receiving engine and registration engine.

The embodiments illustrated and discussed in this specification are intended only to teach those skilled in the art the best way known to the inventors to make and use the invention. Figures are not drawn to scale. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A magnetic resonance imaging (MRI) system, comprising:
    a magnetic resonance imaging scanner;
    a signal processing system in communication with said magnetic resonance imaging scanner to receive a plurality of signals for forming at least one magnetic resonance image of a subject under observation;
    a data storage unit in communication with said signal processing system, wherein said data storage unit contains database data corresponding to a soft tissue region of said subject under observation,
    wherein said database data includes information related to fiber tracts in said soft tissue region of said subject under observation; and wherein said signal processing system is adapted to process said plurality of signals received from said magnetic resonance imaging scanner of said subject under observation to automatically reconstruct at least one soft tissue substructure connecting a plurality of regions of interest of said soft tissue region of said subject under observation using said database data.

2. The magnetic resonance imaging system according to claim 1, wherein said signal processing system is at least partially incorporated within a structure housing said magnetic resonance scanner.

3. The magnetic resonance imaging system according to claim 2, wherein said signal processing system is at least partially incorporated in a workstation that is structurally separate and in communication with said magnetic resonance imaging scanner.

4. The magnetic resonance imaging system according to claim 1, wherein said signal processing system is incorporated in a workstation that is structurally separate from and in communication with said magnetic resonance imaging scanner.

5. The magnetic resonance imaging system according to claim 1, wherein said soft tissue is one of a brain, a heart, a muscle, or combinations thereof.

6. The magnetic resonance imaging system according to claim 1, wherein said information reconstructing at least one soft tissue substructure is obtained from diffusion tensor imaging.

7. The magnetic resonance imaging system according to claim 1, wherein said plurality of signals are associated with at least one of a relaxation time, an apparent diffusion coefficient, a property associated with the diffusion tensor, or combinations thereof.

8. The magnetic resonance imaging system according to claim 1, wherein said database data incorporates data from at least one subject that is different from said subject under observation.

9. The magnetic resonance imaging system according to claim 1, wherein said database data incorporates data from a previous scan of said subject under observation.

10. The magnetic resonance imaging system according to claim 1, wherein said signal processing unit is further adapted to align said database data with said at least one magnetic resonance image of the subject.

11. The system of claim 1, wherein said signal processing system automatically reconstructs said soft tissue substructure by determining which fiber tracts penetrate said plurality of regions of interest using said information related to fiber tracts.

12. The system of claim 11, wherein said information related to fiber tracts includes diffusion tensor imagery.

13. A workstation comprising:
    a receiving engine to receive an atlas having at least one magnetic resonance image corresponding to a soft tissue region having a plurality of soft tissue substructures connecting a plurality of regions of interest in said soft tissue region, and pre-selected data encoding information related to fiber tracts in said soft tissue region; and
    a registration engine to generate database data including information reconstructing said at least one soft tissue substructure by aligning said atlas with said pre-selected data,
    wherein said workstation is in communication with a data storage unit and is adapted to produce database data based on said atlas and said pre-selected data;
    wherein said data storage unit is configured to store said database data that includes the generated identifying information; and wherein said pre-selected data is based on input from at least one experienced operator.

14. A workstation of claim 13, wherein said reconstructing information comprises at least one probabilistic map indicative of the spatial probability of said at least one soft tissue substructure.

15. A workstation of claim 13, wherein registration engine is further configured to:
    store the coordinates reconstructing the at least one soft tissue substructure in alignment with said atlas;
    average the stored coordinates to generate said information reconstructing said at least one soft tissue substructure.

16. The workstation of claim 13, wherein said information reconstructing said soft tissue substructure is generated by determining which fiber tracts penetrate said plurality of regions of interest using said information related to fiber tracts.

17. The workstation of claim 16, wherein said information related to fiber tracts includes diffusion tensor imagery.

18. A workstation to process at least one magnetic resonance image from at least one subject showing a soft tissue region having at least one soft tissue substructure connecting a plurality of regions of interest in said soft tissue region, comprising:
    a receiving engine to receive said at least one magnetic resonance image from said at least one subject and database data including information related to fiber tracts in said at least one soft tissue region;
    an alignment engine to align the received at least one magnetic resonance image with the received database data; and
    a processing engine to generate information reconstructing said at least one soft tissue substructure on the received at least one magnetic resonance image.

19. The workstation of claim 18, further comprising:
    an analysis engine to analyze and output a quantity indicative of a physiological condition within an area on the received at least one magnetic resonance image reconstructed as said at least one soft tissue substructure.

20. The workstation of claim 18, wherein the processing engine is an overlay engine.

21. The workstation of claim 18, wherein the processing engine further generates a display, on a visualization device, information reconstructing said at least one soft tissue substructure as an overlay on said received at least one magnetic resonance image.

22. The workstation of claim 18, wherein said information reconstructing said soft tissue substructure is generated by determining which fiber tracts penetrate said plurality of regions of interest using said information related to fiber tracts.

23. The workstation of claim 22, wherein said information related to fiber tracts includes diffusion tensor imagery.

24. A method comprising:
receiving from a subject at least one magnetic resonance image showing a soft tissue region having at least one soft tissue substructure connecting a plurality of regions of interest in said soft tissue region;
receiving database data related to fiber tracts in said soft tissue region;
aligning said database data with said at least one magnetic resonance image; and
reconstructing said at least one soft tissue substructure using information from said database data and said at least one magnetic resonance image.

25. The method of claim 24, further comprising:
analyzing a quantity indicative of a physiological condition within an area on said magnetic resonance image identified as said at least one soft tissue substructure.

26. The method of claim 25, further comprising determining if said physiologic condition is present based on said indicative quantity.

27. The method of claim 24, wherein reconstructing said soft tissue substructure further comprises determining which fiber tracts penetrate said plurality of regions of interest using said database data related to fiber tracts.

28. The method of claim 27, wherein said database data related to fiber tracts includes diffusion tensor imagery.

29. A non-transitory computer-readable medium comprising software, which when executed by a computer system, causes the computer system to perform operations to generate database data, the software comprising:
one or more instructions to receive an atlas corresponding to a soft tissue region;
one or more instructions to receive data encoding information related to fiber tracts in at least one soft tissue substructure connecting a plurality of regions of interest in said soft tissue region;
one or more instructions to align said data with said atlas; and
one or more instructions to generate database data including information reconstructing said at least one soft tissue substructure.

30. The method of 29, further comprises:
one or more instructions to store the coordinates of the reconstructed at least one soft tissue substructure in alignment with said atlas;
one or more instructions to average the stored coordinates; and
one or more instructions to generate at least one probabilistic map spatially identifying said at least one soft tissue substructure.

31. The method of claim 29, wherein said information reconstructing said soft tissue substructure is generated by determining which fiber tracts penetrate said plurality of regions of interest using said information related to fiber tracts.

32. The method of claim 31, wherein said information related to fiber tracts includes diffusion tensor imagery.

33. A non-transitory computer-readable medium comprising software, which when executed by a computer system, causes the computer system to process at least one magnetic resonance image, the software comprising:
one or more instructions to receive said at least one magnetic resonance from a subject showing a soft tissue region having at least one soft tissue substructure connecting a plurality of regions of interest in said soft tissue region;
one or more instructions to receive database data related to fiber tracts in said soft tissue region;
one or more instructions to align database data with said at least one magnetic resonance image by transforming at least one of shape, size, or orientation of said database data to that of said at least one magnetic resonance image; and
one or more instructions to process information from said database data to reconstruct said at least one soft tissue substructure on said at least one magnetic resonance image.

34. The method of claim 33, further comprising:
one or more instructions to analyze a quantity indicative of a physiological condition within an area on said at least one magnetic resonance image identified as said at least one soft tissue substructure.

35. The method of claim 33, further comprising
one or more instructions to determine if said physiologic condition is present based on said indicative quantity.

36. The method of claim 33, wherein said instructions to process information from said database data to reconstruct said at least one soft tissue substructure further includes instructions to determine which fiber tracts penetrate said plurality of regions of interest using said database data related to fiber tracts.

37. The method of claim 36, wherein said database data related to fiber tracts includes diffusion tensor imagery.

* * * * *